United States Patent [19]

North, Jr.

[11] Patent Number: 4,790,653
[45] Date of Patent: Dec. 13, 1988

[54] HOUSING FOR A FLOW CYTOMETRY APPARATUS WITH PARTICLE UNCLOGGING FEATURE

[75] Inventor: Howard L. North, Jr., Los Gatos, Calif.

[73] Assignee: Becton Dickinson and Company, Franklin Lakes, N.J.

[21] Appl. No.: 866,003

[22] Filed: May 22, 1986

[51] Int. Cl.⁴ .............................................. G01N 15/00
[52] U.S. Cl. ........................................ 356/73; 356/39; 356/336
[58] Field of Search .................... 356/72, 73, 39, 337, 356/336

[56] References Cited

U.S. PATENT DOCUMENTS

| 4,130,754 | 12/1978 | Fosslien | 235/92 |
| 4,526,276 | 7/1985 | Shoor et al. | 209/552 |
| 4,660,971 | 4/1987 | Sage et al. | 356/39 |

Primary Examiner—R. A. Rosenberger
Attorney, Agent, or Firm—Richard J. Rodrick

[57] ABSTRACT

A housing for a particle flow-through apparatus comprises a body member having a passageway therethrough including a region through which substantially one particle at a time may pass in a normal direction of flow. An operative plunger is positioned in the passageway so that the plunger is depressible into the passageway. Depression of the plunger creates increased pressure in the passageway for dislodging clogged particles or debris from the region in a direction reverse to the normal direction of particle flow.

17 Claims, 4 Drawing Sheets

HOUSING FOR A FLOW CYTOMETRY APPARATUS WITH PARTICLE UNCLOGGING FEATURE

BACKGROUND OF THE INVENTION

1. Field of the Invention.

The present invention relates to a housing for a particle flow-through apparatus which includes a particle unclogging feature, and more particularly, concerns a flow cytometry apparatus for determining one or more characteristics of particles flowing through such a housing wherein clogged particles may be removed to facilitate operation of the apparatus.

2. Description of the Prior Art.

There are a number of cell or particle analyzing devices employing flow cytometry techniques which rely on hydrodynamically focused fluid flow through an aperture or orifice for determining specific characteristics of the flowing cells or particles. Flow analysis of particles has been employed in the determination of the variety of characteristics of individual particles. This analysis is most useful in analyzing or determining characteristics of cells for the collection information which would be useful in areas of research, hematology, immunology and the like. The researcher, for example, may be interested in determining specific characteristics of the individual cells so that such cells may be classified, identified, quantified and perhaps sorted for further investigations or analysis.

One commercially available flow cytometry apparatus which relies on a hydrodynamically focused fluid flow system is known as the FACS TM Analyzer sold by the FACS Systems Division of Becton, Dickinson and Company, Mt. View, Calif. The FACS Analyzer rapidly analyzes cells on the basis of fluorescence and electronic volume properties. Analysis is accomplished by introducing cells in suspension to the center of a focused liquid stream and causing them to pass, one at a time, through a filtered and focused light from a high power mercury arc lamp. Each cell is individually characterized by its electronic impedance volume and by the intensity and color of fluorescence emitted while it is illuminated. This analyzer is described in European Pat. No. 0068404. In the aforementioned flow cytometry apparatus, a sheath fluid is utilized to focus the particles or cells as they pass through the orifice associated with the analyzing or counting capabilities. U.S. Pat. Nos. 4,503,385 and 4,526,276 describe particle analysis systems in which particles flowing in a stream are enveloped in a sheath fluid which focuses and confines the sample fluid (with particles or cells) to the center of the flowing stream.

One of the problems which arises when using sheath flow in a hydrodynamically focused fluid system, particularly through a flowcell or flow chamber, is particle clogging. Inasmuch as the particles, such as cells, to be analyzed are typically in the order of 5 to 20 microns in size, the orifice through which these particles pass is very small, especially since the orifice is intended to allow the passage of only one particle at a time. If the sample fluid which contains the particles has cellular debris or particles of irregular size, passage of these materials toward the orifice of the flowcell could cause clogging problems.

In the presently known and available particle flow-through apparatuses, electrically operated high pressure pumps or the like are employed in the fluidics of the system to clean the liquid flow paths including the flowcell orifice and passageways for the particles to be analyzed. The usual operation for these high pressure pumps is to pass cleansing fluid in a direction reverse to the normal particle flow through the apparatus. However, if the particles or debris which clogged the flowcell orifice are clumped together or stuck in a difficult to clean position, the high pressures generated by the electrically operated pump are sometimes not sufficient to expel the debris. If the reverse flow pump does not unclog the orifice, it is usually necessary to take the apparatus apart to clean the individual elements. Reassembly usually requires readjustment and recalibration of optical and electronic elements of the system.

With the foregoing in mind, improved techniques for unclogging passageways in particle flow-through apparatuses are still being sought. Such improvements in a particle unclogging feature should preferably be included in the particle flow-through apparatus so that the various parts of the apparatus do not have to be disassemble din order to unclog the passageways. It is toward such an improvement that the present invention is directed.

SUMMARY OF THE INVENTION

The housing for a particle flow-through apparatus of the present invention comprises a body member having a passageway therethrough including a region through which substantially one particle at a time may pass in a normal direction of flow when the apparatus is operating. Manually operable means is provided to create increased pressure in the passageway for dislodging clogged particles or debris from the region in a direction reverse to the normal direction of particle flow.

In a preferred embodiment of this aspect of the invention, the housing is suitable for a flow cytometry apparatus and includes a body member having a passageway therethrough for the passage of particles which are to analyzed. The passageway includes an analysis portion, a pre-analysis portion and a post-analysis portion. A first channel through the body member is in fluid communication with the pre-analysis portion of the passageway for the introduction of a liquid for ensheathing the particles which flow into the analysis portion of the passageway. A second channel through the body member is in fluid communication with the post-analysis portion of the passageway for the passage of particles and liquids out of the housing after passing through the analysis portion. A plunger has an inner end slidably positioned in fluid-tight engagement in the post-analysis portion of the passageway. An outer end of the plunger extends outwardly of the body member. The plunger is manually depressible within the post-analysis portion to create increased pressure in the passageway for dislodging clogged particles or debris therefrom.

In another aspect of the present invention, a flow cytometry apparatus for determining one or more characteristics of particles or the like flowing in a liquid stream comprises means for moving particles in a liquid flow stream. A body member has a passageway therethrough including a region through which the moving particles pass substantially one at a time in a normal direction of flow. Manually operable means is provided to create increased pressure in the passageway for dislodging clogged particles or debris from the region in a direction reverse to the normal direction of particle flow. Means is included for providing a beam of light to illuminate the particles passing through the region. Means detects light with respect to each moving particle and associates the detected light with one or more characteristics of each particle.

In accordance with the principles of the present invention, a straightforward, simply operated plunger mechanism is built into a housing for inclusion in a particle flow through apparatus such as flow cytometry instrument. The manually operated and depressible plunger permits generation of a high reverse pressure to expel debris from the passageways, including the orifice within the housing. This manually operated plunger serves as a pump to generate high pressures which are required when the debris, such as certain sticky cells or the sticky residue from cell lysis, clogs the passageways. The feature of the present invention for unclogging an orifice or other passageways in the housing is easy to construct, simple to operate and generates sufficiently high pressure to remove clogged debris from the passageways of a particle flow-through apparatus. By including the aforementioned unclogging features in the housing for a particle flow-through apparatus, the unclogging techniques may be performed without disassembling the parts of the apparatus itself. Other advantages of the present invention will be perceived and understood by reading the detailed description which follows below.

DETAILED DESCRIPTION

Figure 1:
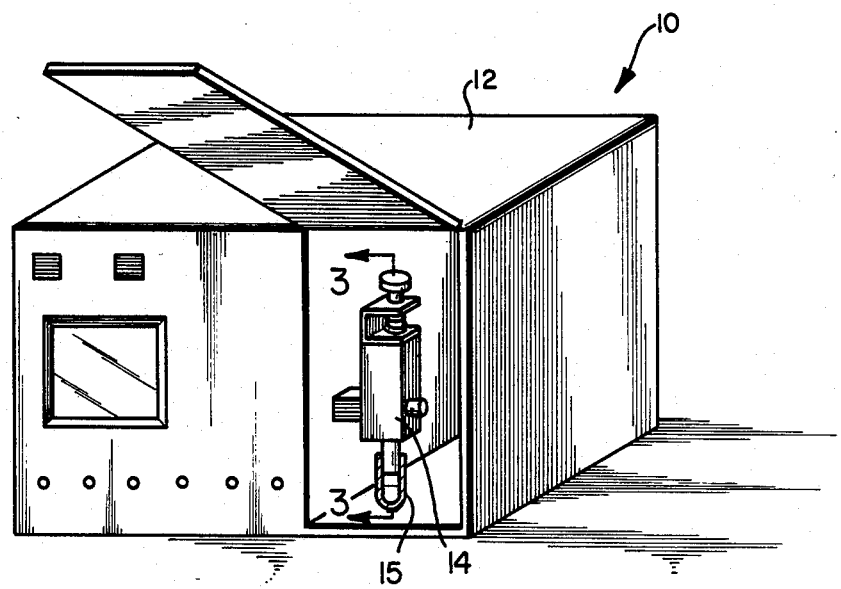
FIG. 1 is a perspective view of one embodiment of a flow cytometry apparatus for determining one or more characteristics of particles or the like flowing in a liquid stream.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings, and FIG. 1 in particular, there is illustrated a flow cytometry apparatus 10 of the present invention for determining one or more characteristics of particles or the like. Apparatus 10, for example, may be a cell analyzer which includes a liquid sampling console 12 which is constructed to contain particle or cell detection and analysis elements as hereinafter described. Liquid sampling console 12 as seen in FIG. 1 includes a flow manifold assembly in the form of a housing 14 which is designed to provide a stream of flowing liquid containing the particle to be analyzed. In the apparatus being described, the particles for analysis may be included in a test tube 15 which may be removably positioned onto housing 14. Before describing the details of housing 14, a general description of the optical and flow elements of flow cytometry apparatus 10 will first be provided.

Figure 2:
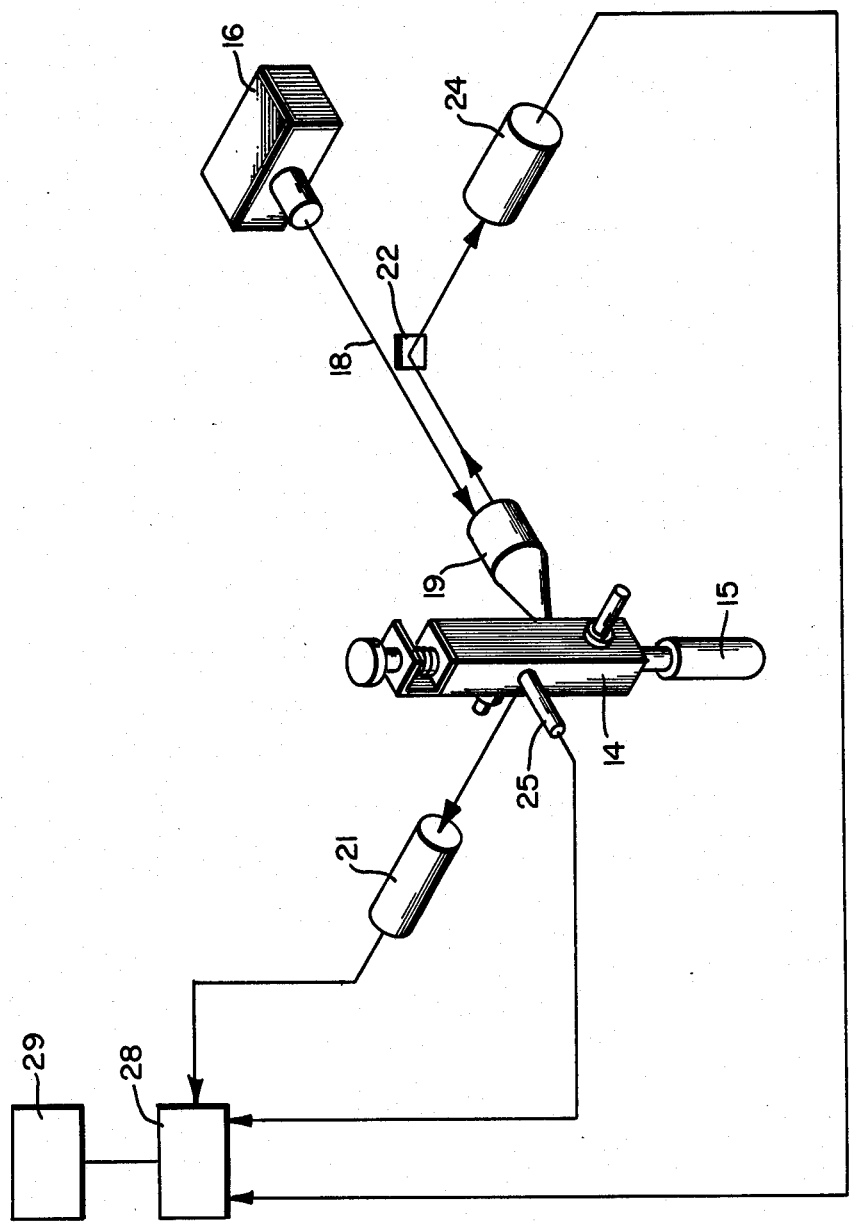
FIG. 2 is a schematic illustration of typical elements and light paths of a flow cytometry apparatus for determining one or more characteristics of particles or the like, embodying the housing of the present invention.

FIG. 2 is a schematic illustration of the general optical and flow elements embodied in a flow cytometry apparatus of the present invention. In addition to the general optical and flow elements of the apparatus to be described below, other details of a cell analyzer apparatus useful in conjunction with the present invention are described in European Pat. No. 0068404. It is understood that the housing of the present invention is useful in many different types of flow cytometry or flow fluorometric apparatuses, which measure light scatter, particle volume, fluorescence or other optical parameters for the identification, quantification or enumeration of cells, particles or the like in a sample liquid medium. As illustrated in FIG. 2, light energy is provided for the flow cytometry apparatus by a light source 16 such as a laser which provides a coherent beam of light at a singular wavelength or an arc lamp, such as a mercury or xenon arc lamp, which provides an incoherent beam of light comprising a broad spectrum of wavelengths.

Excitation energy is provided in the flow cytometry apparatus by a beam of light 18 produced by light source 16. Typically, the beam of light passes through focusing lens 19 which focuses the light beam at the liquid stream containing the particles or cells under investigation, and which will be described in more detail below.

As each cell or particle passes through the focused light region where light beam 18 intersects the flowing liquid stream, light scattered by the cell or particle may be detected by an appropriate photodetector 21. Similarly, fluorescence, if emitted by particles energized by the illumination from the light source may also be detected. Fluorescence emitted by autofluorescent particles or fluorescently labeled or stained particles in the liquid stream may be detected along the same axis as light beam 18 through lens 19, which, may, for example, be a condenser lens assembly. This lens assembly is preferably, but not necessarily, an epi-illuminating system which uses the same lens for imaging excitation light and for receiving fluorescence emission from the particles. Fluorescence emitted by the flowing particles may be directed to a dichroic mirror 22 before being collected by fluorescence detector 24. More than one fluorescence detector may be employed in order to detect fluorescence emitted from the particles at different wavelengths. Photodetector 21 and fluorescence detector 24 may be well-known photomultiplier tubes or similar devices which convert light signals into electrical impulses so that the light thereby detected may be associated with the fluorescently labeled cells and cells of a specific size flowing through the apparatus. In addition, one or more electrodes 25 positioned in the flowing liquid stream may be included for sensing volume of the cells or particles by the well-known Coulter principle. The electrical signals from photodetector 21, fluorescence detector 24 and from electrode 25 are typically fed to the electronics 28 of the apparatus for purposes of display 29, storage or further processing so that one or more characteristics of the cells or particles under analysis may be determined.

Figure 3:
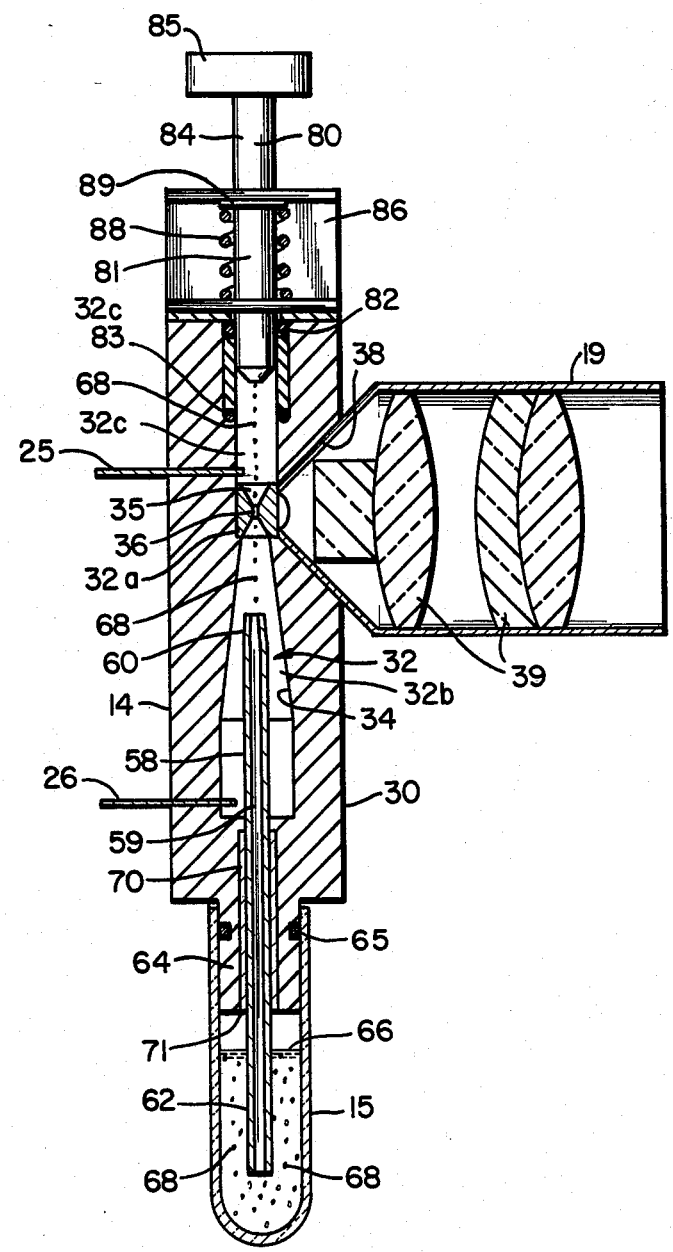
FIG. 3 is an enlarged cross-sectional view of the preferred embodiment of the housing of the present invention taken along line 3—3 of FIG. 1, and also illustrating one embodiment of a lens assembly employed in the optical arrangement of the present invention.
Figure 4:
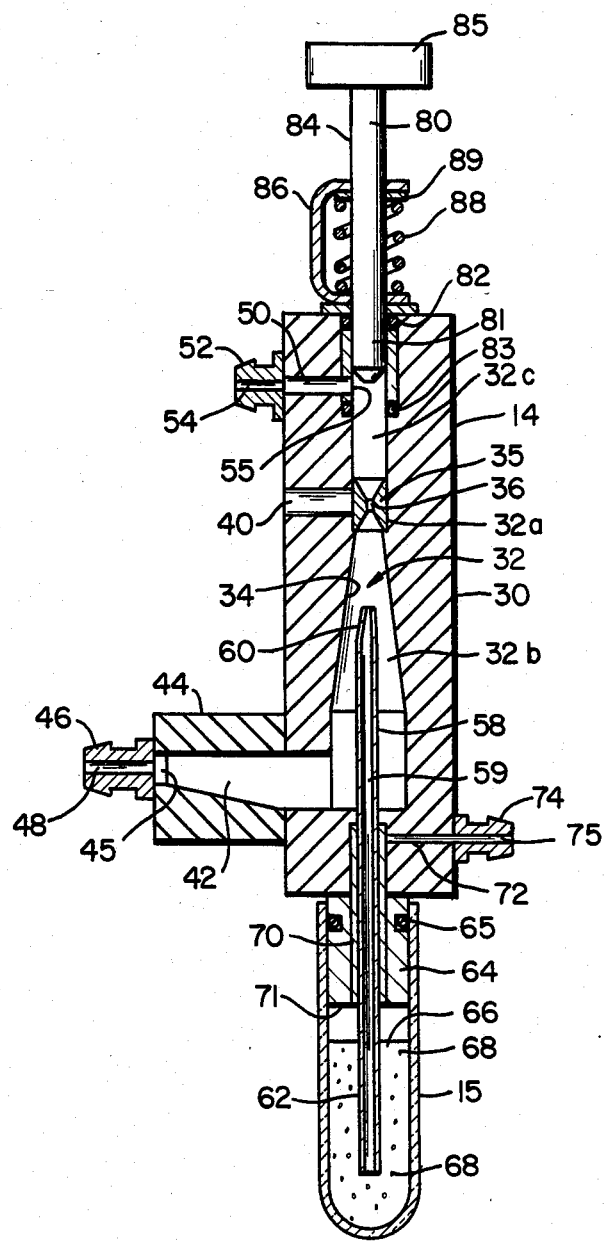
FIG. 4 is an enlarged cross-sectional view of the housing of the present invention illustrated at right angles to the view shown in FIG. 3.

Turning now to FIGS. 3 and 4, the details of housing 14 of the present invention are more clearly illustrated.

It can be seen that housing 14 includes a body member 30 which, in the embodiment being described, is preferably in the form of a block or rectangular prism. Although not shown in the drawings, the block form of housing 14 facilitates the mounting of the housing within the flow cytometry apparatus. Extending through housing 14 is a passageway 32 which is defined by three segments: an analysis portion 32a, a pre-analysis portion 32b, and a post-analysis 32c. As seen in FIGS. 3 and 4, the analysis, pre-analysis and post-analysis portions of passageway 32 lie on the same axis through body member 30.

It is preferred that analysis portion 32a and post-analysis portion 32c of the passageway be cylindrically shaped bores extending into body member 30. On the other hand, it is preferred that pre-analysis portion 32b of the passageway be tapered so that it includes tapered walls 34 defining a frustoconical passageway having its narrow end facing toward analysis portion 32a of the passageway.

Preferably positioned within analysis portion 32a of the passageway is a flowcell or flow chamber 35 which facilitates the analysis of cells or particles under investigation. Flow cell 35 includes an orifice 36 which is preferably sized to permit the passage of substantially one particle at a time therethrough. As a light beam intersects the region defined by orifice 36, particles or cells which pass through the orifice also pass through the light beam thereby establishing a basis for a light-related signal which may be detected in known fashion.

So that light energy may be available to illuminate the region defined by orifice 36 in the flowcell, body member 30 of the housing may include a recess 38 into which lens assembly 19 may be positioned so that the lens assembly lies adjacent flowcell 35. This type of arrangement is illustrated in FIG. 3 and is consistent with a technique known as epi-illumination for providing light energy to interrogate the particles under analysis. Light is directed through lens assembly 19 at an angle substantially orthogonal to the direction of particle flow through the flowcell. Lens assembly 19 may include one or more lenses 39 in a condenser lens assembly for focusing incident light on the particles which pass through orifice 36, and for receiving light such as fluorescence from the particles which have been illuminated by the incident light beam. Of course, the present invention contemplates that light from the particles may be detected in any direction with respect to the axis of the incident light beam. The appropriate light detectors are positioned at the desired angle for collecting light scattered or emitted by the particles or for detecting light energy absorbed by the particles. To this end, one or more windows 40 may extend through body member 30 in line with flowcell 35 through which light may pass for collection by the photodetector elements. On the other hand, it may not be necessary to provide such a window if body member 30 is sufficiently light transmissive to allow light to pass therethrough in sufficient strength to be detected. It is, however, preferred that flowcell 35 be light transmissive and also that the flow cell be removable from body member 30 in the event that it needs replacement or change.

Body member 30 also includes a first channel 42 which is in fluid communication with pre-analysis portion 32b of the passageway. Channel 42, in this embodiment, extends through a side block 44 of body member 30 so that this channel is substantially at right angles to the axis of passageway 32. Side block 44 includes a valve 45, or like device, which is operative to selectively open or close channel 42. Although not shown in FIG. 4, valve 45 may be operated manually, electrically, pneumatically or any other convenient technique of operation. A fluid connector 46 is positioned on side block 44 so that its lumen 48 is in fluid communication with channel 42. It is the purpose of channel 42 to provide a passageway for the introduction of a liquid for ensheathing particles which flow into analysis portion 32a of the passageway, and which more specifically flow through flowcell 35. The provision of a sheath liquid for a hydrodynamically focused fluid flow system is well-known in the art and is described in the aforementioned patents.

Communicating with post-analysis portion 32c of the passageway is another channel 50 which also extends through body member 30 in the embodiment being described. Second channel 50 also extends at substantially right angles to the axis of passageway 32. In fluid communication with channel 50 is a fluid connector 52 having a lumen 54 therethrough. It is the purpose of channel 50 to provide a passageway for the passage of particles and liquids out of housing 14 after passing through the analysis portion of the passageway. It can be seen that channel 50 has its interior end 55 preferably open to post analysis portion 32c of the passageway.

Particles or cells ot be analyzed are preferably transported through a hollow tube 58 with a lumen 59 extending therethrough. Tube 58 extends substantially along the axis of passageway 32 and has an inner end 60 positioned in pre-analysis portion 32b of the passageway. It is preferred that inner end 60 be positioned within tapered walls 34 of the pre-analysis portion so that the inner end of the tube lies adjacent flowcell 35 in the analysis portion of the passageway. Tube 58 has its outer end 62 extending outwardly of body member 30. The body member of the housing preferably includes a circularly shaped extension 64 through which tube 58 extends before passing outwardly of the body member. A gasket 65, or other like element for providing a liquid-tight seal, is positioned around circularly shaped extension 64. It can be seen in FIGS. 3 and 4 that test tube 15 is positioned so that it fits onto extension 64 with gasket 65 facilitating a light-tight seal between the test tube and extension 64 of the body member. Test tube 15 includes sampling liquid 66 and particles 68 to be analyzed. Outer end 62 of the tube extends into sampling liquid 66 in this embodiment.

In order to cause particles 68 in the sampling liquid to be transported into tube 58, an annular passageway 70 is provided around the exterior surface of tube 58. This annular passageway includes an open end 71 surrounding tube 58 at the distal end of extension 64. A third channel 72 extends through body member 30 and is in fluid communication with annular passageway 70. A fluid connector 74 on the side of the body member includes a lumen 75 which is in fluid communication with channel 72. It is the purpose of connector 74 to be connected to a source of pressurized air or other fluid to serve as a driving force of pressure into the test tube so that sampling liquid 66 and particles 68 may pass into lumen 59 of tube 58. Particles 68 pass out of the inner end of the tube into pre-analysis portion 32b of the passageway. Here, the particles and sampling liquid become ensheathed by the sheathing liquid so that the particles may pass substantially one at a time through orifice 36 in flowcell 35, as seen in FIG. 3. Once in the flowcell, the particles may be interrogated by light which enters the flowcell through lens assembly 19 so that light-related information may be determined with respect to each particle. Also, or alternatively, volume-related information about the particles may be determined in conjunction with electrodes 25 and 26 positioned in passageway 32 and which utilize the well-known Coulter principle for volumetric determinations. After the particles, sampling liquid and sheathing liquid pass through the analysis region of the passageway, flow continues through channel 50 for passage out of housing 14. It is appreciated that particles 68 may become clogged in orifice 36, lumen 59 of the tube or other tight areas within the passageway through the housing. The present invention provides a feature for manually unclogging these passageways.

Mounted on body member 30 is a plunger 80 which includes an inner end 81 slidably positioned in fluid-tight engagement in post-analysis portion 32c of the passageway. A sealing gland 82, which may be in the form of or include a gasket facilitates the fluid-tight seal of the plunger within the post-analysis portion of the passageway. A second sealing gland 83 provides a fluid tight seal of the inner end of plunger 81 whenever the plunger is depressed. Outer end 84 of the plunger extends outwardly of the body member and preferably includes a thumb disk or button 85. A preferably U-shaped bracket 86 is provided to support plunger 80 and to facilitate its slidable operation. A coil spring 88 surround plunger 80 and extends between the legs of the U-shaped bracket. Spring 88 is urged against a ring 89 connected to plunger 80. Thus, it can be seen that spring 88 provides a biasing force for urging the plunger in an outward direction when no force of depression is applied to button 85.

On the other hand, it can be seen that button 85 may be manually pushed in a downward fashion so that inner end 81 of the plunger travels inwardly into post-analysis portion of the passageway. When this inward movement of the plunger occurs, open end 55 of channel 50 becomes blocked or closed when plunger 81 engages sealing gland 83. Once the force of manual depression is removed from push button 85, spring 88 actuates the outward movement of the plunger so that channel 50 is once again in open fluid communication with post-analysis portion 32c.

If, during operation of the particle flow-through apparatus, particles become clogged in the passageway, orifice or tube, the manually-operated plunger may be utilized to unclog the passageways. A quick downward thrust against push button 85 creates sufficient reverse pressure in the post-analysis portion of the passageway to dislodge particles which may be clogged in orifice 36. If valve 45, associated with sheathing liquid channel 42, is closed, sufficient reverse pressure may be created to cause the unclogging of lumen 59 of tube 58. The operation of the manually-depressible plunger may be performed while housing 14 is still mounted within the apparatus. The features of the present invention achieve particle unclogging because of the high reverse pressures which may be created. For, example, a force of one pound on a plunger with a diameter of 0.125 inches may produce a pressure of 80 psi in the passageway.

While not shown, it is apparent to those skilled in the art that plunger 80 may be operated by other than manual means, such as an electrical solenoid, a pneumatic piston or similar devices. It is also apparent that inward end 81 of plunger 80 may be provided with a small wire of stiff material, such as tungsten. This wire may be sized and aligned to enter orifice 36 when the plunger is depressed to provide mechanical means for contacting the particles to dislodge them and clean the orifice.

Thus, the present invention provides a housing for a particle flow-through apparatus which includes a particle unclogging feature. The unclogging feature permits the creation of a high reverse pressure of sufficient magnitude to expel debris from an orifice or other small passageways found in these types of apparatuses. Further, due to the features of the present invention, the housing does not need to be removed from the apparatus in order to achieve unclogging of the tight passageways.

What is claimed is:

1. A housing for a flow cytometry apparatus comprising:
   a body member having a passageway therethrough for the passage of particles which are to be analyzed, said passageway including an analysis portion, a pre-analysis portion and a postanalysis portion;
   a first channel extending through said body member for fluid communication with the pre-analysis portion of said passageway for the introduction of a liquid for ensheathing said particles which flow into the analysis portion of said passageway;
   a second channel extending through said body member for fluid communication with the post-analysis portion of said passageway for the passage of particles and liquids out of said housing after passing through said analysis portion; and
   a plunger having an inner end slidably positioned in fluid-tight engagement in said post-analysis portion of said passageway and an outer end extending outwardly of said body member, said plunger being depressible within said post-analysis portion so that said inner end closes said fluid communication of said second channel with said post-analysis portion of said passageway thereby blocking the flow of liquids and particles from said housing through said second channel to create increased pressure in said passageway post-analysis portion for dislodging clogged particles or debris from said analysis portion.

2. The housing of claim 1 wherein the analysis portion of said passageway includes a flowcell having an orifice sized to permit the passage of substantially one particle at a time through said analysis portion, whereby depression of said plunger creates sufficient reverse pressure in said post-analysis portion to dislodge particles clogged in said orifice.

3. The housing of claim 2 wherein said body member includes means for permitting light to be directed at said orifice at an angle substantially orthogonal to the direction of particle flow through said flowcell.

4. The housing of claim 3 wherein said means for permitting light includes a recess for positioning a lens adjacent said flowcell.

5. The housing of claim 1 wherein the pre-analysis, analysis and post-analysis portions of said passageway lie on the same axis through the body member.

6. The housing of claim 5 which further includes a tube having an inner end positioned in said pre-analysis portion of said passageway and an outer end extending outwardly of said body member, said tube having a lumen extending therethrough for the passage of particles toward the analysis portion of the passageway.

7. The housing of claim 6 wherein said pre-analysis portion includes a tapered segment which narrows toward said analysis portion, the inner end of said tube being positioned within said tapered segment adjacent the analysis portion.

8. The housing of claim 5 wherein said first and said second channels extend into said body on axes different from said passageway axis.

9. The housing of claim wherein said plunger inner end includes mechanical means for contacting said particles in said analysis portion to dislodge clogged particles or debris when said second channel is closed to fluid flow when said plunger is depressed within said post-analysis portion.

10. The housing of claim 1 wherein said plunger includes means for moving the plunger in an outward direction after the force of manual depression is removed from the outer end of said plunger.

11. The housing of claim 10 wherein said means for moving is a spring for biasing the plunger in an outward direction when no force of depression is applied to the outer end of the plunger.

12. The housing of claim 1 which further includes valve means for closing said first channel so that, upon depression of said plunger, increased pressure is applied to the lumen of said tube for dislodging clogged particles or debris from said tube.

13. A housing for a particle flowthrough apparatus comprising:
   a body member having a passageway therethrough including an analysis region through which substantially one particle at a time may pass from a pre-analysis portion to a post-anlysis portion in the direction of particle movement with the liquid flow stream when said apparatus is operating; and
   operative means including a member for sealingly engaging said post-analysis portion of said passageway for closing said post-analysis portion thereby blocking the flow of liquid and particles through said post-analysis portion to create increased pressure in a direction reverse to said direction of particle movement with the liquid flow stream in said passageway for dislodging clogged particles or debris from said analysis region.

14. The housing of claim 13 wherein said operative means are manually operative.

15. The housing of claim 13 wherein said operative means includes structure for contacting the clogged particles or debris in order to dislodge same from said region.

16. A housing for a flow cytometry apparatus comprising:
   a body member having a passageway therethrough for the passage of particles which are to be analyzed, said passageway including an analysis portion, a pre-analysis and a post-analysis portion, all of which lie on the same axis through said body member;
   a tube having an inner end positioned in said pre-analysis portion of said passageway adjacent the analysis portion and an outer end extending outwardly of said body member, said tube having a lumen extending therethrough for the passage of said particles toward the analysis portion of said passageway;
   a flowcell included in said analysis portion and having an orifice sized to permit the passage of substantially one particle at a time through said analysis portion;
   a first channel extending through said body member for fluid communication with the pre-analysis portion of said passageway for the introduction of a liquid for ensheathing said particles which flow into the analysis portion of said passageway;
   a second channel extending through said body member for fluid communication with the post-analysis portion of said passageway for the passage of particles and liquids out of said housing after passing through said analysis portion,
   a plunger having an inner end slidably positioned in fluid tight engagement in said post-analysis portion of said passageway and an outer end extending outwardly of said body member, said plunger being depressible into said post-analysis portion when said flow cytometry apparatus is not operating to close said second channel to prevent fluid flow between said second channel and the post-analysis portion and to create sufficient pressure in the post-analysis portion of said passageway for dislodging clogged particles or debris in said orifice, said plunger including a spring for biasing the plunger in an outward direction when no force of manual depression is applied to the outer end of said plunger; and
   a valve positioned in said first channel to close said first channel upon depression of said plunger and increased pressure in said orifice.

17. A flow cytometry apparatus for determining one or more characteristics of particles or the like flowing in a liquid stream comprising:
   means for moving particles in a liquid flow stream;
   a body member having a passageway therethrough including an analysis region through which said moving particles pass substantially one at a time in the direction of particle movement with the liquid flow stream;
   cooperative means including a member for sealingly engaging said passageway for closing said passageway beyond said analysis region thereby blocking the flow of liquid and particles through a post-analysis portion to create increased pressure in a direction reverse to said direction of movement with the liquid flow stream in said passageway for dislodging clogged particles or debris from said analysis region;
   means for providing a beam of light to illuminate said particles passing through said analysis region; and
   means for detecting light with respect to each moving particles and for associating said detected light with one or more characteristics of each particle

* * * * *